(12) United States Patent
Jiang et al.

(10) Patent No.: US 8,048,262 B2
(45) Date of Patent: *Nov. 1, 2011

(54) RAPID FATTY ACID ASSAY FOR USE IN PULP PITCH CONTROL

(75) Inventors: Chengliang Jiang, Duluth, GA (US); Xiang H. Wang, Alpharetta, GA (US); Jianhua Ma, Alpharetta, GA (US); Robin M. Yezzi, Smyrna, GA (US)

(73) Assignee: Enzymatic Deinking Technologies, LLC, Norcross, GA (US)

( * ) Notice: Subject to any disclaimer, the term of this patent is extended or adjusted under 35 U.S.C. 154(b) by 391 days.

This patent is subject to a terminal disclaimer.

(21) Appl. No.: 12/137,255

(22) Filed: Jun. 11, 2008

(65) Prior Publication Data

US 2008/0236770 A1   Oct. 2, 2008

Related U.S. Application Data

(60) Continuation of application No. 11/534,117, filed on Sep. 21, 2006, now abandoned, and a continuation-in-part of application No. 11/378,755, filed on Mar. 17, 2006, now abandoned, which is a division of application No. 10/126,173, filed on Apr. 19, 2002, now Pat. No. 7,067,244.

(60) Provisional application No. 60/285,259, filed on Apr. 20, 2001.

(51) Int. Cl.
*D21C 9/00* (2006.01)

(52) U.S. Cl. ........................................................... 162/9

(58) Field of Classification Search ................ 162/9, 49, 162/71, 72, 158, 199, 198; 73/53.03
See application file for complete search history.

(56) References Cited

U.S. PATENT DOCUMENTS

| | | |
|---|---|---|
| 4,301,244 A | 11/1981 | Kikuchi et al. |
| 4,743,339 A | 5/1988 | Faix et al. |
| 5,176,796 A | 1/1993 | Irie et al. |
| 5,256,252 A | 10/1993 | Sarkar et al. |
| 5,293,219 A | 3/1994 | Ayer |
| 5,667,634 A | 9/1997 | Fujita et al. |
| 5,989,392 A | 11/1999 | Tang et al. |
| 7,067,244 B2 | 6/2006 | Jiang et al. |
| 2003/0046984 A1 | 3/2003 | Jiang et al. |
| 2003/0124710 A1* | 7/2003 | Borch et al. .................. 435/262 |
| 2007/0261806 A1* | 11/2007 | Wang et al. .................... 162/32 |

FOREIGN PATENT DOCUMENTS

WO    WO 02/086230    10/2002

* cited by examiner

*Primary Examiner* — Mark Halpern
(74) *Attorney, Agent, or Firm* — Pabst Patent Group LLP

(57) ABSTRACT

Methods are provided for determining the surface fatty acid content in a wood pulp or whitewater sample. The methods comprise reacting free fatty acids which are present on the surface of the wood pulp fibers in the sample or in the whitewater with one or more reagents to form a measurable species, and determining the fatty acid content from the quantitative measurement of the measurable species. The method is useful as a quick, portable, accurate and low cost assay for assessing the fatty acid content present at various sample points in pulp and paper mills. The method for determining the free fatty acid content can be conducted in a batch process (e.g., where samples are collected periodically and the test is conducted offline). Alternatively, the method for determining the free fatty acid content can be conducted in a continuous or semi-continuous process (e.g., online sampling/analysis).

18 Claims, 1 Drawing Sheet

RAPID FATTY ACID ASSAY FOR USE IN PULP PITCH CONTROL

This application is a continuation of pending prior application Ser. No. 11/534,117 filed Sep. 21, 2006, entitled "Rapid Fatty Acid Assay for Use in Pulp Pitch Control", by Chengliang Jiang, Xiang H. Wang, Jianhua Ma, and Robin M. Yezzi and is also a continuation-in-part application of U.S. Ser. No. 11/378,755 filed on Mar. 17, 2006, which is a divisional of Ser. No. 10/126,173, filed on Apr. 19, 2002, now U.S. Pat. No. 7,067,244, which claims priority under 35 U.S.C. 119 to U.S. Ser. No. 60/285,259, filed on Apr. 20, 2001, all of which are herein incorporated in their entirety by reference.

FIELD OF THE INVENTION

The method described herein is generally in the field of diagnostic tools for pitch control in pulp and paper mill processes.

BACKGROUND OF THE INVENTION

Minimizing or preventing the deposit of pitch in pulp and paper making processes is critical to minimizing equipment fouling and paper machine down time, maximizing production efficiency, and improving product quality. Pitch is composed of low molecular weight olephilic materials (primarily triglycerides, fatty acids, terpenes, resin acids and esters), which are released from wood fibers during chemical and mechanical pulping processes. These resinous substances usually precipitate as calcium and magnesium salts, causing problems with the wet end components of paper machines.

Known methods for pitch control include cationic fixation with cationic polymers, dispersion with surfactants, absorption with talc, and chelation with heavy metals. Enzymatic methods also are known. For example, U.S. Pat. No. 5,176,796 to Irie, et al, discloses adding acylglycerol lipase to mechanical pulp paperstock or reuse water. U.S. Pat. No. 5,256,252 to Sarkar et al. discloses adding a lipase and a cationic polymer to a papermaking cellulosic slurry. U.S. Pat. No. 5,667,634 to Fujita et al. discloses adding a water-soluble polyelectrolyte to increase the hydrolysis rate of esters in the presence of a lipase.

Effectively employing these and other pitch control methods, however, requires an accurate assessment of the quantity of depositable pitch present in the pulp and process waters throughout several points in the papermaking process. Standard diagnostic techniques for measuring pitch include a test to measure the total organic extractive content of the pulp. Unfortunately, known methods of total organic extractive content determinations, fatty acid analysis, or triglyceride analysis of pulp take between about 8 and 24 hours to complete. Therefore, the test results are useful only for post evaluation of the process system; they do not provide an assessment of the current state of the process, and yield unreliable and unfocused results. Accordingly, use of analytical methods to accurately apply pitch control measures is quite limited, as the dynamic nature of the pitch level in a continuous papermaking process requires a timely response with the pitch control strategies. It would be highly advantageous to have a method that analyzes the triglyceride and/or fatty acid content of the pulp quickly and accurately so that process parameters can be adjusted to timely and accurately prevent pitch deposition problems.

One current method of triglyceride analysis is based on the analysis of fatty acids produced by the hydrolytic reaction of triglyceride in the presence of lipase:

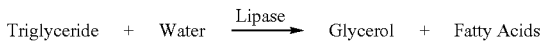

The method steps include (1) analyzing the fatty acid content of a first pulp sample that has not been treated with enzyme using an extraction, evaporation, and titration procedure; (2) calculating the percent of organic acid as oleic acid for the first sample; (3) treating a second pulp sample with a high dose of enzyme under conditions to ensure complete conversion of triglyceride to fatty acids and glycerol; (4) analyzing the fatty acid content of the enzyme-treated second pulp sample using the extraction, evaporation, and titration procedure; and (5) comparing the difference of organic acid in the first sample and the second sample. The triglyceride content is determined by the difference of fatty acid content before and after lipase treatment of the pulp sample, multiplied by a conversion factor. The conversion factor is the ratio of the molecular weight of the triglycerides to the molecular weight of the fatty acids. It is assumed that at high lipase dosage, the triglycerides are converted entirely to fatty acids and glycerol. No side reactions occur.

Various methods have been proposed for free fatty acid analysis. One method is that free fatty acid is first extracted with one or more organic solvents. The extensive extraction, evaporation, and titration by alkali procedures required to assess fatty acid content are time consuming and labor intensive. For example, the fatty acids in the pulp sample are extracted into a hexane layer and aliquots of the hexane layer then are evaporated, leaving an organic residue that subsequently is dissolved into an aqueous isopropanol solution, which is then titrated with potassium hydroxide solutions using thymol blue as a pH indicator. Due to the multiple steps involved, there exists the problem of poor reproducibility with this method as well as the time it takes to complete the procedure.

Another method for free fatty acid analysis also involves an extensive solvent extraction step followed by a high cost instrumental analysis step, involving high performance liquid chromatography (HPLC), thin layer chromatography (TLC), or gas chromatography (GC). These extraction-based methods typically take between about 8 and 24 hours to complete, require the use of potentially dangerous volatile organic compounds or toxic solvents, and are very labor intensive. The instrumental analysis is not portable for on site analysis, and the results often are inaccurate or irreproducible. It would be advantageous to have an accurate test method that does not require the extraction step, so that the pulp could be tested directly and rapidly. Such a test preferably would be portable, fast and easy to use, without high cost instrumental analysis. It would be beneficial if the method also minimized or eliminated the tester's potential exposure to volatile organic compounds or toxic solvents required by the extraction-based methods.

Pitch on the surface of the pulp fibers or in the suspension, i.e. the depositable pitch, is the greatest concern in pitch deposition in pulping and paper manufacturing mills. Total pitch consists of pitch located on the surface of the fibers and pitch trapped within the pulp fibers. The pitch trapped within the fibers generally does not contribute to the pitch deposition problem, as it remains intact within the fibers and does not have a chance to deposit. Therefore, a test method providing results that directly correlate to pitch depositions problems would be highly beneficial.

U.S. Pat. No. 7,067,244 "Rapid Triglyceride Assay for Use in Pulp Pitch Control" Jiang et al. describes enzymatic methods for determining the surface triglycerides content in a wood pulp sample. The methods comprise reacting triglycerides which are present on the surface of the wood or in the whitewater in the presence of a lipase to form glycerol and fatty acids, and then determining the difference between the amount of free glycerol present in the sample and the amount of glycerol formed from the triglycerides.

Gaining such an understanding of fatty acid concentration can be quite valuable since fatty acids can create much broader problems than triglycerides. Fatty acids are a component of the natural extractives of wood pulp. The concentration of free fatty acids in the pulp is a function of the species of trees used, the maturity of the tree, growing conditions, harvesting season, the debarking process, the storage of the wood and seasoning/aging of the wood, and, more important, the pulping method used in the pulp production. In mechanical pulping which uses little or no chemicals, only limited chemical changes occur to the wood extractives and their relative distribution. However, in chemical (kraft) pulping, the extractives are subjected to intensive chemical reactions, therefore both the chemical composition and relative distribution of wood extractives change substantially. For example, during the cooking stage with the pH near 14, wood extractives react with strong caustic chemicals. Therefore, glycerides are converted to fatty acids, and then the fatty acids are saponified to fatty soaps. In the bleaching stages, strongly oxidative chemicals, such as $ClO_2$, $H_2O_2$, and $O_3$, will then oxidize unsaturated fatty acids. Therefore, kraft pitch is fundamentally different from mechanical pitch.

Moreover, many treatments used in the pulping of recycled fiber, such as deinking, involve fatty-acid-based chemicals, either fatty acids or fatty soaps. Some of the chemicals will be carried over to the papermaking process. Naturally occurring fatty acids, fatty acids generated from the triglyceride conversion by lipase enzyme, and the carry over of fatty acid-based chemicals can cause problems with the wet end components of paper machines if they are not managed properly. At present, the management of fatty acids generated from enzyme conversion is difficult to do. This is chiefly due to the lack of an effective tool for quantitatively monitoring the generation, flow, distribution, and accumulation of fatty acids in the system.

Therefore, it would be desirable to provide methods, devices, and kits for accurately and rapidly determining the fatty acid content of a pulp sample, particularly for use in a continuous papermaking process. It would also be desirable to provide methods for enhancing the effectiveness of pitch control measures in a papermaking process based on such determinations. It would further be desirable to provide methods for measuring the surface and/or colloidal fatty acids in wood pulp, wherein the test is portable, fast and easy to use without high cost instrumental analysis, and minimizes or eliminates the tester's potential exposure to volatile organic compounds or toxic solvents required by extraction-based total organic content diagnostic assays.

Therefore, it is an object of the invention to provide methods, devices, and kits for accurately and rapidly determining the fatty acid content of a pulp sample, particularly for use in a continuous papermaking process.

It is further an object of the invention to provide methods for enhancing the effectiveness of pitch control measures in a papermaking process based on such determinations.

It is a further an object of the invention to provide methods for measuring the surface and/or colloidal fatty acid content in wood pulp, wherein the test is portable, fast and easy to use without high cost of instrumental analysis, and minimizes or eliminates the tester's potential exposure to volatile organic compounds or toxic solvents required by extraction-based total organic content diagnostic assays.

BRIEF SUMMARY OF THE INVENTION

Methods for determining the fatty acid concentration in a pulp stock or water sample are described herein. The methods are useful for rapidly assessing the amount of triglycerides present at various sample points in pulp and paper mills, which advantageously serves as a diagnostic tool for use in controlling the undesirable deposition of pitch during the pulping and paper making process. The methods advantageously can be conducted at low cost using portable equipment, if desired. The method for determining the fatty acid content in a wood pulp or whitewater sample comprises (1) reacting the free fatty acids in the sample in one or more reactions to form a measurable species; and (2) determining the concentration of the fatty acids from a quantitative measurement of the measurable species. The quantitative measurement can be obtained from a test measuring a property such as concentration of an electrochemical species, spectrometric characteristics, or chromatographic characteristics. In a preferred embodiment, the measurable species is a colored substrate and the quantitative measurement is obtained spectrophotometrically. The method for determining the free fatty acid content can be conducted in a batch process (e.g., where samples are collected periodically and the test is conducted offline). Alternatively, the method for determining the free fatty acid content can be conducted in a continuous or semi-continuous process (e.g., online sampling/analysis).

The method for determining the triglyceride content in a pulp sample through the above-mentioned free fatty analysis includes the steps of (1) analyzing the free fatty acid content of the pulp sample; (2) analyzing the free fatty acid content of the same pulp sample treated with excess amount of lipase to convert triglceride into fatty acids and glycerol; and (3) comparing the difference of the free fatty acid in the two samples before and after lipase treatment. The triglyceride content is determined by the free fatty acid difference, multiplied by a conversion factor. Kits containing the reagents needed to assay depositable triglycerides are also described herein.

The methods described herein can be used to enhance the effectiveness of pitch control measures. Methods for pitch control include cationic fixation with cationic polymers, dispersion with surfactants, absorption with talc, and chelation with heavy metals. Enzymatic methods also are known. For example, U.S. Pat. No. 5,176,796 to Irie, et al. discloses adding acylglycerol lipase to mechanical pulp paperstock or reuse water. U.S. Pat. No. 5,256,252 to Sarkar et al. discloses adding a lipase and a cationic polymer to a papermaking cellulosic slurry. U.S. Pat. No. 5,667,634 to Fujita et al. discloses adding a water-soluble polyelectrolyte to increase the hydrolysis rate of esters in the presence of a lipase.

DETAILED DESCRIPTION OF THE INVENTION

Figure 1:
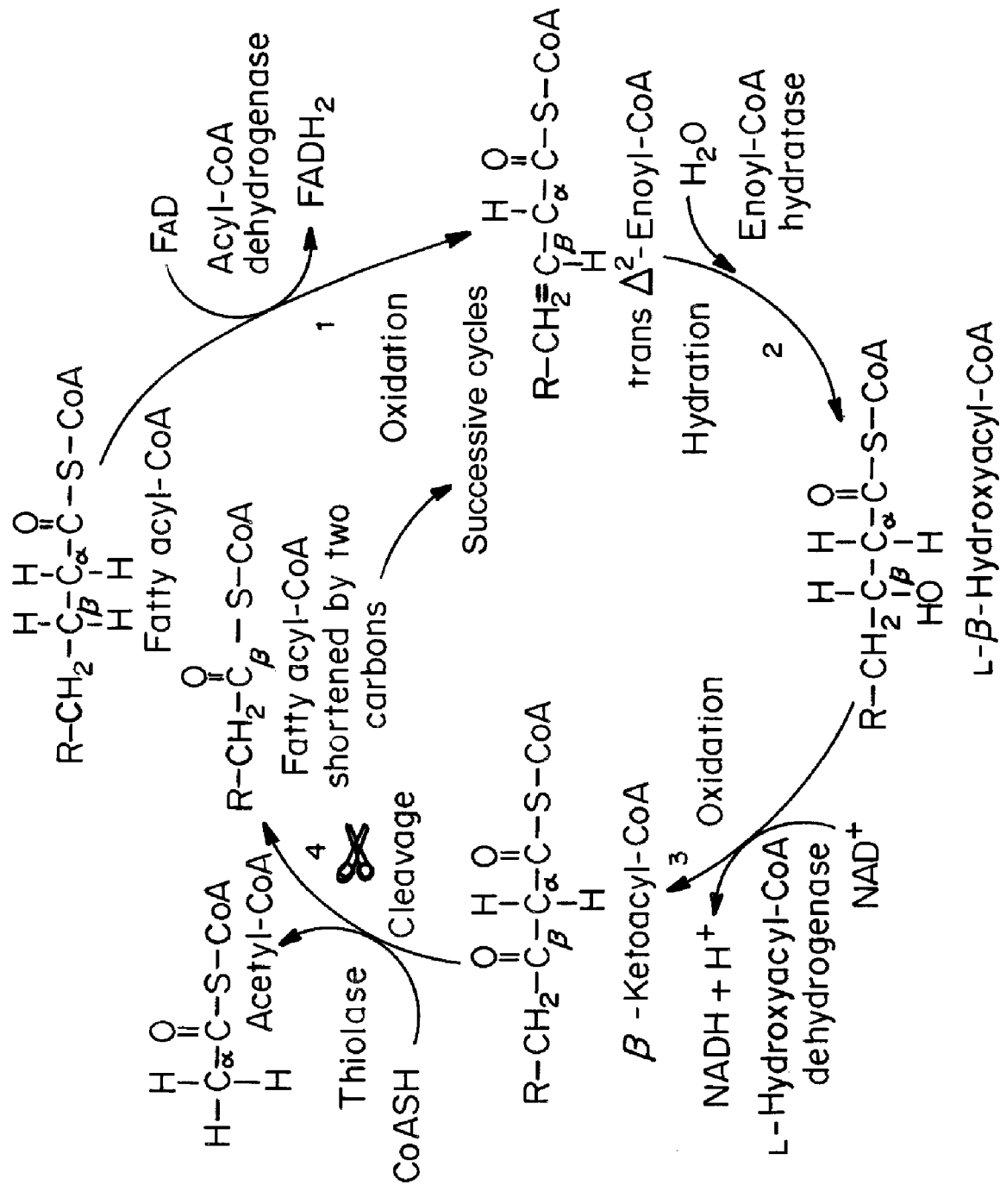
FIG. 1 is a schematic representation of the β-oxidation of fatty acids.

Methods for determining the surface or colloidal fatty acid content in a wood pulp or whitewater sample are described herein. The fatty acid content can be measured at various sample points in paper mills for use in predicting and controlling pitch deposition on paper machine components.

I. Definitions

As used herein, the term "depositable triglycerides" refers to triglycerides residing on the surface of the pulp fibers as well as free triglycerides suspended in the process water with the pulp fibers or free triglycerides present in process water from which pulp fibers have been separated, such as whitewater. This is in contrast to the total triglycerides, which includes triglycerides trapped within the pulp fibers, which typically do not contribute to pitch deposition, but which are included in the total organic extractive content of the pulp. There can commonly be a poor correlation between the quantity of trapped or total triglycerides and the amount of pitch deposition observed.

As used herein, the term "free fatty acids" refers to fatty acids residing on the surface of the pulp fibers as well as free fatty acids suspended in the process water with the pulp fibers or free fatty acids present in process water from which pulp fibers have been separated, such as whitewater. This is in contrast to the total fatty acids, which includes fatty acids trapped within the pulp fibers, which typically do not contribute to pitch deposition, but which are included in the total organic extractives content of the pulp. There can commonly be a poor correlation between the quantity of trapped or total fatty acids and the amount of pitch deposition observed.

As used herein, the term "wood pulp sample" includes wood fiber suspensions, wood fibers, paper fibers, defibered waste paper, and process water taken from essentially any sampling points in a pulping or paper manufacturing mill, which may or may not contain wood or paper fibers.

II. Methods for Analyzing Free Fatty Acid Content

In one embodiment, the method for determining the fatty acid content in a wood pulp sample includes the steps of (1) reacting the free fatty acids in a wood pulp sample in one or more reactions to form a measurable species; and (2) determining the fatty acid content in the sample from the quantitative measurement of the measurable species. A variety of methods that have been developed to assay for fatty acids in biological applications can also be adapted for use in assaying for fatty acids as described herein. For example, U.S. Pat. No. 4,301,244 to Kikuchi et al. describes a method for the quantitative analysis of free fatty acids in blood.

Similar, but different, methods can be used as a diagnostic tool to analyze paper machine deposition problems online as they occur because of the substantially shorter assay time as compared to currently used, extraction-based methods. The fatty acid assay can be conducted in preferably less than 6 hours, more preferably less than 4 hours, even more preferably less than 2 hours, and most preferably less than 1 hour (e.g., less than 30 minutes, less than 20 minutes).

The method for determining the fatty acid content can be conducted in a batch process (e.g., where samples are collected periodically and the test is conducted offline). Alternatively, the method for determining the fatty acid content can be conducted in a continuous or semi-continuous process (e.g., online sampling/analysis).

A. Wood Pulp and Sample Points

The fatty acid analytical methods described herein can be applied to any essentially wood pulp sample taken from essentially any sampling points in the pulping or paper manufacturing mills. The sampling point can be any point in the mill where pitch problems may exist. Representative examples of sample points include, but are not limited to, the low density chest (LD), which is a storage chest for pulp; the high density chest (HD), which is another storage chest for pulp; the decker, which thickens the pulp; the whitewater sample, which is a sample of the water inside the system loop; the blend chest; the headbox, which is the location just before the paper machine where the stock is prepared for the paper making process; whitewater chests, and the paper machine (PM) where the paper is actually made. In recycling mills, examples of sample points include, but are not limited to, the pulper, dump chest, flotation cells, washers, bleaching stages, associated stock and water tanks of deinking plant equipment, water treatment systems, and the stock and water samples around the paper machine.

These methods are particularly useful in pulping and paper manufacturing mills that use a mechanical pulp. The methods are also useful with other pulps, such as Kraft and other chemical pulps.

B. Measurement of the Free Fatty Acid Concentration

The step of obtaining a quantitative measurement of the measurable species can be performed using a variety of different techniques and reaction sequences. These techniques are desirably conducted rapidly, simply, accurately, and at low cost. In one embodiment, the step is highly automated and suitable for use in continuous or semi-continuous diagnostic equipment. In another embodiment, the step is conducted as a batch process, for example, in which pulp samples are collected periodically and tested offline (e.g., periodic manual sampling and then field or laboratory testing of these samples).

In one embodiment, the measurement of the fatty acid content includes the steps of (a) reacting the free fatty acids in the wood pulp sample in one or more reactions to form a measurable species, in which the fatty acids present in the wood pulp sample are a reactant, (b) obtaining a quantitative measurement of the measurable species; and (c) determining the fatty acid content from the quantitative measurement of the measurable species.

In one embodiment, the method is an enzyme-based colorimetric method that uses a spectrophotometer for detection. It generally takes only between about 20 and 30 minutes to assay a set of samples using such a method. The results are accurate and reproducible, and the method advantageously does not require use of the volatile organic compounds and solvents needed for use with extraction-based methods. The method also measures the fatty acid content in the pulp and in the water, which relates to pitch deposition problems.

In another embodiment, non-colorimetric methods are used to determine the fatty acid content in a wood pulp sample. Representative examples of non-colorimetric methods employ tests based on turbidities, titrations, impacts of electrical current arrays, or spectroscopic methods such as GC, HPLC, and NMR.

C. Fatty Acid Detection

A variety of reaction sequences can be used to convert the free fatty acids to a quantifiable, measurable species. For example, the quantitative measurement can be obtained from a test measuring a property selected from concentration of an electrochemical species, spectrometric characteristics, and chromatographic characteristics.

In one embodiment, the fatty acids are enzymatically reacted in a reaction sequence that produces the measurable species. For example, the fatty acids are reacted with coenzyme A (CoA) and adenosine triphosphate (ATP) to form acyl-coenzyme A (acyl-CoA), adenosime monophosphate (AMP), and pyrophosphate. The acyl-CoA is then enzymatically oxidized with an electron acceptor.

Examples of electron acceptors include oxygen ($O_2$), nicotinamide adenine dinucleotide ($NAD^+$), and nicotinamide adenine dinucleotide phosphate ($NADP^+$). Certain indolphenols, potassium ferricyanide, and certain tetrazolium salts can also be used as electron acceptors. In one embodiment, Acyl-CoA is reacted with oxygen ($O_2$) to form enoyl-CoA and hydrogen peroxide. The hydrogen peroxide is then reacted with any one of a variety of dye precursors to produce a measurable color change, which can be quantified for example using a spectrophotometer. For example, a quinoneimine dye can be produced by reacting the hydrogen peroxide with 4-amino antipyrine (4-AA) and a hydrogen donor (chromogen) which develop color in the presence of a peroxidase. As the calorimetric method, the following peroxidase chromogen may be used (a) 4-AA and 2,4,6-tribromo-3-hydroxybenzoic acid (TBHB) to form a red color, which may be detected at 546 nm; (b) 4-AA and 3-methyl-N-ethyl-N-(β-hydroxyethyl)-aniline (MEHA) to form a purple color, which may be detected at 550 nm; (c) 4-AA and phenol to form a red color, which may be detected at 505 nm; (d) 3-methyl-2-benzothiazolinone hydrazone (MBTH) and dimethylaniline (DMA) to form a blue color, which may be detected at 590 nm; and (e) 4-AA and DMA or diethylaniline (DEA) to form a purple color, which may be detected at 550 nm, in the presence of a peroxidase.

The absorbance analysis can be conducted using essentially any commercially available spectrophotometer operable at a useful wavelength. The spectrophotometer preferably is portable, such as the HACH DR/2000 or DR25001. In an alternative embodiment, the methods described herein can be adapted to measure transmittance (which is related to absorbance) and the fatty acid content calculated accordingly.

Assay (1)

In this embodiment, the assay utilizes the following enzyme-coupled reactions:

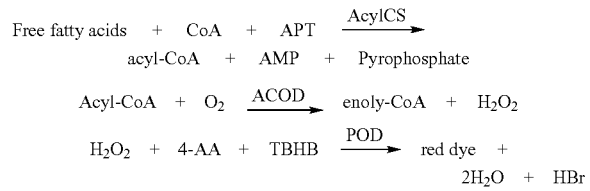

The free fatty acids on fibers and in fiber suspensions are reacted with co-enzyme A (CoA) and adenosine triphosphate (ATP) in the presence of acyl-CoA synthetase (Acyl CS) to form adenosine-5'-diphosphate (AMP) and acyl-coenzyme A (Acyl-CoA). Acyl-CoA reacts with an electron acceptor, such as oxygen, in the presence of acyl-coenzyme A oxidase (ACOD), to form 2,3-enoyl-coenzyme A (Enoyl-CoA) and hydrogen peroxide. The peroxide reacts with 4-aminoantipyrine and 2,4,6-tribromo-3-hydroxybenzoic acid (TBHB) to form a red dye and water.

From this series of reactions, the concentration of the dye formed as the final product is directly proportional to the concentration of the fatty acids initially present in the sample and can be detected with a spectrophotometer. In a preferred embodiment, absorbance is measured at a wavelength of 546 nm, which is the optimum wavelength where absorbance is at its maximum value, but a range of other wavelengths, e.g., between about 500 and 580 nm, can also be used.

Assay (2)

This assay is based on the complete degradation of long chain fatty acids through enzymatic β-oxidation. The reaction scheme is shown schematically in FIG. 1.

Reaction 1: Formation of fatty acyl-CoA by acyl-CoA synthetase (EC 6.2.1.3)

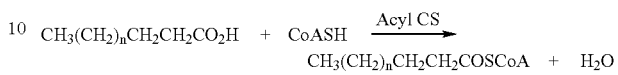

Reaction 2: Oxidation of fatty acyl-CoA by acyl-CoA dehydrogenase (EC 1.3.99.3) to form enoyl-CoA

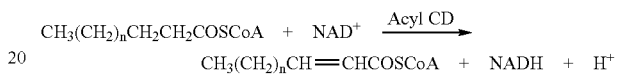

Reaction 3: Hydration of enoyl-CoA by enoyl-CoA hydrolase (EC 4.2.1.17) to form 3-hydroxylacyl-CoA

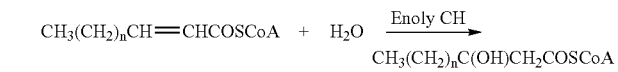

Reaction 4: Oxidation of 3-hydroxyacyl-CoA by 3-hydroxylacyl-CoA dehydrogenase (EC 1.1.1.35) to form 3-ketoacyl-CoA

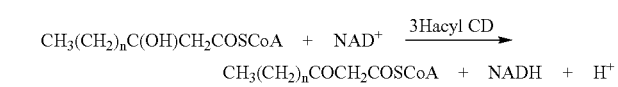

Reaction 5: Hydrolysis of 3-ketoacyl-CoA by 3-ketoacyl-CoA thiolase (EC 2.3.1.16) to form acetyl-CoA and a fatty acid acyl-CoA, which is two carbons less than the initial fatty acid starting material

Each round of the process results in the formation of one molecule of acetyl-CoA and a fatty acyl-CoA, which is two carbons shorter than the initial starting material. The fatty acyl-CoA continually re-enters the cycle until the fatty acid has been completely degraded into acetyl-CoA and NADH.

For example, the overall reaction of stearic acid oxidation can be described as follows:

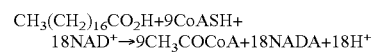

For each mole of stearic acid that is oxidized, nine moles of acetyl-CoA and 18 moles of NADH will be produced. The concentration of NADH can be measured directly at 340 nm using a UV spectrophotometer.

Alternatively, NADH can be measured colormetrically via the following coupling reactions using 2-(p-iodophenyl)-3-(p-nitrophenyl)-5-phenyl tetrazolium chloride (INT):

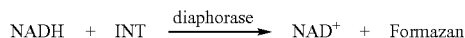

Formazan has a sharp absorption peak at 500 nm (pink color). Note that each mole of stearic acid produces 18 moles of NADH, which in turn form 18 moles of formazan. The absorption of NADH is extremely strong, at least 18 times the values observed in Assay (1). Assay (2) should be a more sensitive assay than Assay (1).

III. Kits for Use in Conducting the Assays

In one embodiment, five reagents are prepared for use in the assay: (1) Bottle 1: a solution of pH 7.8 phosphate buffer of 11 mL; (2) Bottle 2: a tablet containing ATP, coenzyme A, acyl-CoA synthetase (Acyl CS), peroxidase, ascorbate oxidase, 4-aminoantipyrine and stabilizers; (3) Bottle 3: an N-ethylmaleimide solution with a stabilizer (N-ethylmaleinimide is necessary for the removal of any excess CoA before the oxidation of the activated fatty acids by ACOD); (4) Bottle 4: a dilute solution of acyl-CoA oxidase (ACOD) and a stabilizer of 0.6 mL; and (5) Bottle 5: tablets of acyl-CoA oxidase (ACOD). The reagents preferably are provided as a kit of parts to perform the claimed assay. These kits may further include assay equipment, such as test tube vials, filters, syringes, water bath, pipettes, timers, and/or a spectrophotometer. The five reagents are preferably stored at a temperature between 2 and 8° C.

These materials are available commercially. For example, some of the reagents can be obtained from Roche's free fatty acids, half-micro test available from Roche Applied Science, Indianapolis, Ind. The following table lists the concentrations for each component in Roche's testing kit and the suitable concentration ranges in one tablet or solutions.

TABLE 1

Concentration of each component and their ranges

| Bottle no. | Testing kit | Most preferred concentration | Preferred concentration | Suitable concentration |
|---|---|---|---|---|
| 1 | Phosphate buffer 7.8 | 0.05 mM | 0.02-1.0 mM | 0.01-2.0 mM |
| 2 | ATP | 30 | 5-50 | 2-200 |
|   | Coenzyme A | 6 | 3-10 | 2-25 |
|   | Peroxidase | 500 U | 20-1000 | 5-2000 |
|   | Ascorbate oxidase | 30 | 10-50 | 5-100 |
|   | 4-aminoantipyrine | 3 | 1-5 | 1-15 |
|   | Surfactant |   |   |   |
| 3 | N-ethyl-maleinimide | 25% | 5-50 | 1-100 |
| 4 | Buffer MOPS-NaOH | 25 | 10-50 | 2-100 |
| 5 | Acyl-CoA oxidase (ACOD) | 100 | 50-200 | 15-300 |

The reagent compositions in bottles 2, 3 and 4 preferably are stabilized with a non-reactive stabilizer, such as sorbitol or propylene glycol, and preserved with a preservative, such as sodium azide at a concentration of 0.05% and a surfactant, such as Triton X-100 at a concentration of 0.1%.

The reagents described above can be combined to make two solutions: solution A and solution B. Solution A is prepared by dissolving one tablet from Bottle 2 (coenzyme A/Acyl CS) in Bottle 1 (phosphate buffer). Solution B is prepared by dissolving one tablet from Bottle 5 (acyl-coenzyme A oxidase) in Bottle 4 (dilute solution of ACOD and stabilizer). The solutions are stable for up to 5 days if stored at temperatures between 2 and 8° C. in the dark In other embodiments, peroxidase, TBHB, and 4-aminoantipyrine can be substituted with functionally equivalent materials. The peroxidase catalyzes the oxidation of a chromogen of peroxidase in the presence of hydrogen peroxide. Examples of other substances that are not peroxidases, but possess peroxidase-like activity include, but are not limited to, iron sulfocyanate, iron tannate, ferrous ferrocyanide, and chromic salts absorbed in silica gel. TBHB and 4-aminoantipyrine combine with hydrogen peroxide in the presence of peroxidase to produce a red dye.

Chromogens of peroxidase are color-forming substrates, which produce a color change in the presence of hydrogen peroxide and peroxidase. Representative examples of peroxidase chromogens include monoamines, such as aniline and its derivatives; diamines, such as ortho-phenylenediamine, dianisidine, and benzidine; phenols such as thymol; polyphenols such as catechol; aromatic acids such as salicyclic acid; leuco dyes such as leucomalachite green; and colored dyes such as 2,6-dichlorophenolindophenol.

The present invention will be further understood by reference to the following non-limiting examples.

EXAMPLES

Example 1

Free Fatty Acid Analysis Procedure Using Roche's Testing Kit for Pulp Samples

To determine the absorbance of a pulp stock sample ($A_S$), 1.00 mL of Solution A was pipetted into a capped test tube. 0.50 mL of pulp and 0.5 mL of water were also added to the capped test tube. The contents of the test tube were mixed, the test tube was heated to 25° C., and the contents were reacted for 10 minutes. After 10 minutes, 50 μL of Bottle-03 was added to the test tube and the contents were mixed well. The reaction was initiated by adding 0.05 mL of Solution B to the test tube with mixing. The contents were reacted for 15 minutes in a 25° C. water bath. 1.00 mL of distilled water was added to the test tube. The supernatant obtained by centrifuge and/or filtration of the reacted pulp sample was measured at 546 nm using water as the blank.

To determine the absorbance of water ($A_O$), 1.00 mL of Solution A was pipetted into a capped test tube followed by 1.0 mL of distilled water. The contents of the test tubes were mixed, the test tube was heated to 25° C., and the contents were reacted for 10 minutes. After 10 minutes, 50 μL of Bottle-03 was added to the test tube and the contents were mixed well. The reaction was initiated by adding 0.05 mL of Solution B to the test tube with mixing. The contents were reacted for 15 minutes in a 25° C. water bath. 1.00 mL of distilled water was added to the test tube. The sample was measured at 546 nm using water as the blank.

The free fatty acid (FFA) content is measured using the following equation:

$$\% FFA = \frac{\Delta A}{K_{pulp}} * \frac{1}{100} * \frac{1}{C}$$

wherein $\Delta A = A_S - A_0$ ($A_S$ is the absorbance of the pulp stock sample and $A_0$ is the absorbance of water); $K_{pulp}$ is a constant, depending on the pulp fiber characteristics, waters in the pulp sample and their composition, and the type of dyes formed in the reaction, buffer solution and detection equipment. C is the consistency of the sample, expressed as a percentage.

Alternatively, the free fatty acid (FFA) was measured in part per million (ppm) based on the wet pulp using the following equation:

$$FFA(ppm) = \frac{\Delta A}{K_{pulp}} * DF$$

wherein DF is the dilution factor.

Example 2

Measurement of the Free Fatty Acid Content of Standard Solutions in Distilled Water Fatty acid standard solutions were prepared in the following manner. 6.0 g of Triton X100 was dissolved in about 80 ml of double distilled water (30-40° C.). The solution was cooled to 15-25° C. and diluted to 100 ml in a graduated cylinder.

The desired amount of a fatty acid (i.e. oleic acid) was dissolved in about 6 ml of warm ethanol (about 35-40° C.) in a 100 mL beaker. The beaker was immediately sealed with Parafilm and cooled to 15-25° C.

To prepare the standard solutions, approximately 80 ml of the Triton X100 solution was added to the solution of the fatty acid, with stirring, to avoid the formation of microcrystals at the point of initial mixing. The solution was stirred for an additional 30 minutes using a magnetic stirrer and then transferred quantitatively to a 100 ml volumetric flask and diluted to the mark.

The testing procedure is the same as described in Example 1. The results in Table 2 show the absorbance at 546 nm of different oleic acid standard solutions. The absorbance versus oleic acid concentration exhibited a linear relationship at the oleic acid concentration tested.

TABLE 2

Absorbance of Different Oleic Acid Standard Solutions

| Test No. | Total volume mL | 200 mg/L Oleic acid added, mL | OA Conc. in 0.5 mL soln, mg/L | Abs at 546 nm |
|---|---|---|---|---|
| 1 | 3.1 | 0.00 | 0 | 0.016 |
| 2 | 3.1 | 0.05 | 20 | 0.235 |
| 3 | 3.1 | 0.10 | 40 | 0.470 |
| 4 | 3.1 | 0.20 | 80 | 0.918 |

Example 3

Measurement of the Free Fatty Acid Content for Pulp Samples Taken at Different Sample Locations The free fatty acid test described herein was used for analyzing the free fatty acid profile in a newsprint mill process where lipase enzyme was used for converting triglyceride into free fatty acid to control pitch deposition. The enzyme was added at the decker accept. The samples in the process roughly follow a similar order in the table. The free fatty acid analysis procedure is the same as described in Example 1. The results are given in Table 3.

TABLE 3

Results of the Free Fatty Acid Analysis of Pulp Samples From Newsprint Mill A.

| Sample | Pulp Consistency, % | Abs Reading at 546 nm | FFA, % |
|---|---|---|---|
| Latency Chest | 3.37 | 0.022 | 0.06 |
| TMP Whitewater | 0.11 | 0.021 | 0.50 |
| Decker Accept | 4.64 | 0.417 | 1.10 |
| Low Density Chest | 4.29 | 0.222 | 0.58 |
| PM whitewater | 0.54 | 0.356 | 1.73 |
| Headbox 1 | 1.05 | 0.361 | 0.90 |
| Headbox 2 | 1.27 | 0.521 | 1.08 |
| Tray silo 1 | 0.50 | 0.314 | 1.65 |
| Tray silo 2 | 0.59 | 0.315 | 1.40 |

It can be seen from Table 3 that the latency chest sample before lipase enzyme addition contained little fatty acid, while other samples after lipase enzyme addition showed very high free fatty acid contents. The analysis method makes it possible to profile the FFA distribution in the process and to help identify problems associated with free fatty acids in the paper making process.

Example 4

Measurement of the Free Fatty Acid Content of Pulp Samples Treated at Different Lipase Concentration The free fatty acid content of pulp samples was measured using the procedure as described in Example 1. The results of these measurements are shown in Table 4.

TABLE 4

Results of Free Fatty Acid Analysis of a Decker Feed Pulp Sample Treated at Different Lipase Concentrations

| Test No. | Lipase added, ppm | Triglyceride Content, % | Abs Reading for FFA test | % FFA Measured | % FFA Calculated based on TG Conversion |
|---|---|---|---|---|---|
| 0 | 0 | 1.63 | 0.178 | 0.47 | 0.47 |
| 1 | 250 | 0.93 | 0.446 | 1.17 | 1.14 |
| 2 | 500 | 0.73 | 0.524 | 1.38 | 1.33 |
| 3 | 1000 | 0.55 | 0.590 | 1.55 | 1.51 |
| 4 | 2000 | 0.31 | 0.648 | 1.70 | 1.73 |

Table 4 shows the test results of a decker feed pulp sample from a newsprint Mill A's thermomechanical pulping process after treatment with lipase at different concentrations at 65° C. for 2 hours. The triglycerides in the pulp were converted into glycerol and free fatty acids. As lipase enzyme dosage increased, the triglyceride (TG) content in the pulp decreased and the free fatty acid content should increased. The last two columns in Table 4 indicated that the free fatty acid contents measured with the current method were very close to the free fatty acid calculated based on the triglyceride conversion. This demonstrated that the free fatty acid analysis method described herein is reliable, accurate and consistent with the triglyceride testing.

Example 5

Measurement of the Free Fatty Acid Content of Market Kraft, Newsprint Pulp and Recycled Pulp The free fatty acid content of pulp samples was measured using the procedure as described in Example 1. The results of these measurements are shown in Table 5.

TABLE 5

Free Fatty Acid Analysis of Kraft pulps, recycling pulps and market newsprint.

| Mills | Pulp and paper samples | Absorbance at 546 nm | Free Fatty Acid Content, % Based on O.D. fibers |
|---|---|---|---|
| B | Softwood Kraft Pulp | 0.015 | 0.060 |
| B | Hardwood Kraft Pulp | 0.015 | 0.060 |
| C | 100% Recycled Newsrpint | 0.021 | 0.042 |
| D | TMP Newsprint | 0.038 | 0.076 |
| E | TMP Newsprint | 0.026 | 0.052 |
| E | TMP Newsprint | 0.067 | 0.134 |
| F | 100% Recycled Mixed Office Waste Paper | 0.016 | 0.064 |
| G | 70% ONP/30% OMG Deinked Pulp | 0.066 | 0.071 |

Table 5 shows the free fatty acid analysis for pulp and paper samples from kraft pulp, recycling paper and market newsprint. The results indicated that TMP newsprint has the highest fatty acid content compared with other pulp and paper products.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for determining fatty acid content in wood pulp samples, the method comprising
    reacting free fatty acids in a wood pulp sample to form a measurable species; and
    determining the concentration of the fatty acids from a quantitative measurement of the measurable species.

2. The method of claim 1 wherein the wood pulp sample is selected from wood fibers, wood fiber suspensions, paper fibers, defibered waste paper, and process waters which may contain wood or paper fibers.

3. The method of claim 1 wherein the quantitative measurement of the measurable species is obtained by measuring a property selected from the group consisting of concentration of an electrochemical species, spectrometric characteristics, and chromatographic characteristics.

4. The method of claim 3, wherein the measurable species is a colored substrate and the measurement is obtained spectrophotometrically.

5. The method of claim 1, wherein the free fatty acids are converted to acyl-coenzymes A.

6. The method of claim 5, wherein the acyl-coenzymes A are enzymatically oxidized with an electron acceptor.

7. The method of claim 6, wherein the acyl-coenzymes A are reacted with oxygen ($O_2$) to form enoyl-coenzymes A and hydrogen peroxide.

8. The method of claim 7 wherein the hydrogen peroxide is reacted with a dye precursor to produce a measurable color change.

9. The method of claim 8, wherein the reaction of the hydrogen peroxide with the dye precursor produces a dye.

10. The method of claim 9, wherein peroxidase catalyzes the oxidation of a chromogen of peroxidase in the presence of hydrogen peroxide.

11. The method of claim 9, wherein the hydrogen peroxide is reacted with 4-aminoantipyrine and a compound selected from the group consisting of 2,4,6-tribromo-3-hydroxybenzoic acid (TBHB), 3-methyl-N-ethyl-N-(β-hydroxyethyl)-aniline (MEHA), phenol, 3-methyl-2-benzothiazolinone hydrazone (MBTH), dimethylaniline (DMA) and DMA or diethylaniline (DEA) and 2-(p-iodophenyl)-3-(p-nitrophenyl)-5-phenyl tetrazolium chloride (INT), in the presence of a peroxidase.

12. The method of claim 11 wherein the compound is 2,4,6-tribromo-3-hydroxybenzoic acid.

13. The method of claim 3, wherein the chromatographic characteristics are obtained from a test selected from the group consisting of high performance liquid chromatography, gas chromatography, thin layer chromatography, nuclear magnetic resonance imaging, mass spectroscopy, flame ionization detection, and gas-liquid chromatography.

14. The method of claim 1 conducted on-line.

15. The method of claim 1 conducted in a batch process.

16. The method of claim 1 conducted in a continuous or semi-continuous process.

17. A method for enhancing pitch control in a pulp and paper mill comprising:
    (a) obtaining one or more wood pulp samples from a sampling point in a pulp and paper mill;
    (b) assaying for depositable triglycerides in said one or more wood pulp samples, by reacting depositable triglycerides in a wood pulp sample in the presence of a lipolytic enzyme to form fatty acids and comparing the amount of fatty acids present in the wood pulp sample before treatment with the lipolytic enzyme with the amount of fatty acids present in the wood pulp sample after treatment with the lipolytic enzyme; and
    (c) implementing one or more pitch control methods as needed based on the results obtained in step (b), wherein the pitch control measure is selected from the group consisting of cationic fixation, surfactants dispersion, talc adsorption, heavy metal chelation and enzymatic treatment.

18. A method for determining the triglyceride content in a pulp sample, the method comprising:
    (1) analyzing free fatty acid content of the pulp sample;
    (2) analyzing free fatty acid content of the same pulp sample treated with excess amount of lipase to convert triglyceride into fatty acids and glycerol; and
    (3) calculating the triglyceride content by comparing the difference of the free fatty acid in the two samples before and after lipase treatment.

* * * * *